US006932809B2

(12) United States Patent
Sinofsky (10) Patent No.: US 6,932,809 B2
(45) Date of Patent: Aug. 23, 2005

(54) SAFETY SHUT-OFF DEVICE FOR LASER SURGICAL INSTRUMENTS EMPLOYING BLACKBODY EMITTERS

(75) Inventor: Edward L. Sinofsky, Dennis, MA (US)

(73) Assignee: CardioFocus, Inc., Norton, MA (US)

( * ) Notice: Subject to any disclaimer, the term of this patent is extended or adjusted under 35 U.S.C. 154(b) by 202 days.

(21) Appl. No.: 10/145,866

(22) Filed: May 14, 2002

(65) Prior Publication Data

US 2003/0216720 A1 Nov. 20, 2003

(51) Int. Cl.[7] .............................................. A61B 18/18
(52) U.S. Cl. ............................ 606/12; 606/10; 606/11; 606/15; 606/16; 250/336.1; 250/338.1; 374/100
(58) Field of Search ................................. 606/7, 10–18; 250/336.1, 338; 374/100

(56) References Cited

U.S. PATENT DOCUMENTS

| | | | | |
|---|---|---|---|---|
| 4,311,142 A | * | 1/1982 | Machida ...................... | 606/12 |
| 4,385,832 A | * | 5/1983 | Doi et al. ................... | 356/73.1 |
| 4,476,512 A | * | 10/1984 | Sunago et al. ............... | 361/103 |
| 4,543,477 A | | 9/1985 | Doi et al. | |
| 4,663,520 A | | 5/1987 | Tanaka et al. | |
| 4,730,885 A | | 3/1988 | Doi | |
| 4,812,641 A | | 3/1989 | Ortiz Jr. | |
| 4,883,054 A | * | 11/1989 | Fuller et al. ................... | 606/12 |
| 4,896,141 A | | 1/1990 | Farquhar et al. | |
| 4,994,059 A | * | 2/1991 | Kosa et al. ..................... | 606/12 |
| 5,012,087 A | | 4/1991 | Rockstroh et al. | |
| 5,057,099 A | | 10/1991 | Rink | |
| 5,064,271 A | | 11/1991 | Kern et al. | |
| 5,104,391 A | * | 4/1992 | Ingle et al. .................... | 606/11 |
| 5,154,707 A | * | 10/1992 | Rink et al. ..................... | 606/12 |
| 5,499,313 A | | 3/1996 | Kleinerman | |
| 5,928,222 A | * | 7/1999 | Kleinerman .................. | 606/16 |
| 6,514,277 B1 | * | 2/2003 | Lilge et al. .................... | 607/88 |

FOREIGN PATENT DOCUMENTS

EP 212786 A1 * 3/1987 ........... A61B/17/36

OTHER PUBLICATIONS

Sinofsky, E. and Roth, L. "Safety Interlocking Laser Output Prior to Optical Fiber Burnback," *SPIE–Optical Fibers in Medicine and Biology*, 576: 51–54 (1985).

Farr, N. and Sinofsky E. "Infrared Techniques for Detecting Carbonization at Onset of Device Failure," *SPIE Proceedings*, 2970: 507–512 (1997).

U.S. Appl. No. 09/713,586, Sinofsky et al.

Sinofsky, E. "Comparative Thermal Modeling of Er:YAG, Ho:YAG and $CO_2$ Laser Pulses For Tissue Vaporization," *SPIE–Lasers in Medicine*, 712: 188–192 (1986).

* cited by examiner

*Primary Examiner*—A. Farah
(74) *Attorney, Agent, or Firm*—Thomas J. Engellenner; Deborah A. Miller; Nutter McClennen & Fish LLP (57) ABSTRACT

Methods and systems are disclosed for detecting overheating in an optical device before harmful consequences, such as severe local heating, can result. In one embodiment of the invention, a blackbody emitter is disposed in close proximity to a therapeutic optical fiber to absorb therapeutic radiation at a fault and re-emit blackbody (infrared) radiation. The emitter can be coupled to the fiber but, during normal operation, lies outside the optical path between the output of the laser radiation and the site of treatment. Systems and catheters incorporating such emitters are also described for effective monitoring of the laser power transmitted along the optical fiber within the phototherapy device.

50 Claims, 11 Drawing Sheets

SAFETY SHUT-OFF DEVICE FOR LASER SURGICAL INSTRUMENTS EMPLOYING BLACKBODY EMITTERS

FIELD OF THE INVENTION

The technical field of the present invention is phototherapy and, in particular, the monitoring of a phototherapy device for possible failure during the delivery of laser energy.

BACKGROUND OF THE INVENTION

Optical fibers are used as remote delivery systems for high-powered laser energy and have become invaluable in a wide range of medical applications and in the treatment of a variety of diseases. When used in the treatment of blocked arteries, for example, many benefits are achieved, such as the acceleration of the healing process and the discouragement of scar tissue, by the cauterizing properties of the transported radiation. Laser energy conducted through a flexible waveguide, such as an optical fiber, has been used successfully for photocoagulation, hypothermic therapies, photoactivation of drugs and various other procedures.

Optical fibers are one of the most practical ways to deliver high powered radiation with very little loss of energy. The low attenuation is achieved by encasing the optical fiber in a polymer coating, or cladding. However, there are certain limitations to the use of optical fibers. Optical fibers are delicate—making them prone to breakage by excessive bending, shock or high temperatures. If the fiber breaks, radiation is released at the fault site which can quickly lead to melting or photodecomposition of the polymer coating surrounding the fiber as well as the instrument in which the fiber is encased. In addition, the fault can result in exposure of the patient and/or the clinicians to injurious high-energy radiation. When used in percutaneous operations, the energy transmitted through the fiber is often at a sufficient level that a break in the fiber can cause significant damage to blood vessels and surrounding tissue.

To prevent catastrophic device failures while delivering phototherapeutic energy during laser procedures, mechanisms for detecting failure are needed. It is desirable for the operator to determine and to be reasonably confident that the laser energy being directed to the treatment site is within certain predetermined desirable limits, that is, the energy is known to exceed a certain base or minimum therapeutic level, while not exceeding a certain upper limit. An indication that the laser beam energy is within a predetermined range enables the procedure to be more reliable, expedient, reproducible, and efficacious.

Moreover, it is highly desirable to have control systems that can detect problems in laser phototherapy before the problems become dangerous to the patient and/or destructive to the treatment apparatus. An automated monitoring system, and interlocked switch for shutting off the laser beam as the power fiber begins to fail, would satisfy a long felt need in the art. Currently available methods used to detect optical fiber faults have serious shortcomings including lack of sensitivity and inefficiency in detecting optical faults which allow considerable damage to occur (e.g., charring or combustion of polymeric tubing materials) before a signal is generated.

One known approach is to monitor radiation that propagates back through the treatment fiber (or a parallel transmission path) to detect changes in infrared radiation ("blackbody radiation") that would indicate overheating of the instrument somewhere along the optical path. However, optical fiber cladding generates only small amounts of blackbody radiation until it undergoes chemical decomposition, and thus systems that rely on optical feedback can allow a significant amount of radiation to be released prior to signaling a shut-off protocol.

The present invention is directed to solving the technical problem of providing improved sensitivity in the detection of overheating, quick feedback, and continuous monitoring so that a better shut-off device for laser energy delivery systems is achievable.

SUMMARY OF THE INVENTION

Methods and systems are disclosed for detecting overheating in an optical device before harmful consequences, such as severe local heating, can result. In one embodiment of the invention, a blackbody emitter is disposed in close proximity to a therapeutic optical fiber to absorb therapeutic radiation at a fault and re-emit blackbody (infrared) radiation. The emitter can be coupled to the fiber but, during normal operation, lies outside the optical path between the output of the laser radiation and the site of treatment. Systems and catheters incorporating such emitters are also described for effective monitoring of the laser power transmitted along the optical fiber within the phototherapy device.

In one aspect of the invention, the emitter absorbs radiation generated at a fault and efficiently re-emits blackbody radiation back to the optical fiber. The emitter acts as a conduit for detecting a break, discontinuity, or excessive microbend in the fiber and signals by blackbody radiation feedback that a fault in the optical device has occurred. Changes in the intensity of the blackbody radiation, resulting, for example, from a fault in the optical assembly, can be continuously monitored. Beam splitters and/or various filtering devices are disclosed for separating blackbody radiation generated at the fault site from reflected radiation at the therapeutic wavelength to maximize the signal to noise ratio and minimize the scatter in detected radiation caused by the therapeutic procedure itself. An automatic shut-off protocol can be triggered once the change in intensity of the blackbody radiation reaches a preset limit.

In another aspect of the invention, a method of fault detection in the therapeutic laser device is disclosed wherein the heat generated at a break in the optical device is absorbed and emitted by an emitter as blackbody radiation, which gets transmitted back along the optical fiber to a detector.

In one embodiment, the emitter of blackbody radiation may comprise a discrete element, such as a wire bonded to the optical fiber or spiraled around the optical fiber. In another embodiment, the emitter is incorporated into the buffer coating of the optical fiber (e.g. metal-filled buffer). In a third embodiment, a set of conductive elements, such as a collection of braided metallic fibers that form a jacket around the optical fiber or another component of the optical assembly, is incorporated into the optical assembly.

In yet another embodiment of the invention, the optical device is contained within a catheter having one or more inner lumens. In one embodiment, the emitter is contained within the same lumen as the solution. In another embodiment, the emitter is separate from the solution. The solution, for example, may be used for irrigation or cooling.

Another aspect of the invention is to disclose signal processing circuitry whereby blackbody radiation from a phototherapy device is monitored by comparing the measured blackbody radiation transmitted through the metallic conductor with a predetermined value. A warning or control signal is generated when the measured signal exceeds the threshold value. The control system could then be used, for example, to automatically shut-off the device.

The predetermined threshold value can be set by the user, or automatically generated, or empirically determined by a start-up protocol or dynamically adjusted. In a preferred embodiment, the threshold is adjusted to account for changes in the detector's sensitivity due to temperature changes in the detector itself over time.

The present invention is also advantageous over the relatively insensitive existing shut-off mechanisms for laser surgical systems, which are not responsive to the initial signs of local heating and allow considerable damage to occur (e.g., charring or combustion of polymeric tubing materials) before a signal is generated. Fault detection sensitivity is greatly enhanced in the present invention since an increase in the intensity of the blackbody radiation absorbed by and efficiently emitted from the emitter could be detected by the control module at a much lower temperature.

BRIEF DESCRIPTION OF THE DRAWINGS

The invention will be more fully understood from the following detailed description taken in conjunction with the accompanying drawings, in which.

DETAILED DESCRIPTION

The present invention is directed to optical systems combined with blackbody emitters that have mechanisms for monitoring and shutting down a therapeutic laser before device failure. The systems are adapted for both new and existing laser systems to enhance the effectiveness of laser surgical delivery systems by alleviating the risk of damage to the delivery system due to the increased power. Overall, the optical system provides a simple, reliable, safety shut-off device for optical systems. The practice of the present invention employs, unless otherwise indicated, conventional methods of optics, laser technology, and conduction physics.

The present invention is based, at least in part, on a discovery that a blackbody can be adapted to be used as an efficient monitoring conduit for therapeutic radiation. Blackbody radiation, preferably at wavelengths ranging from about 1.1 micrometers to about 2.2 micrometers, is a useful indicator of changes in optical elements, especially plastic components such as fluoropolymer housings, jackets, lenses and the like (Farr & Sinofsky. SPIE Proc. 2970: 507–512 (1997); Sinofsky & Roth. SPIE-Optical Fibers in Medicine and Biology. 576: 51–54 (1985)). Changes in such plastic and fluoropolymer components could provide a warning of potential hazards and delivery system failures. The teachings of U.S. patent application Ser. No. 09/713,586, filed Nov. 15, 2000, entitled "Safety Switches for Medical Laser Systems," are incorporated herein by reference. However, serious damage would have occurred prior to that warning signal. Therefore, an object that effectively and efficiently absorbs and emits blackbody radiation could provide an earlier warning of such failures prior to damage to the surgical instrument.

An object that absorbs all of the energy incident on it (i.e., an ideal absorber) and emits as much radiation as it absorbs is referred to as a "blackbody," and the radiation it emits is called blackbody radiation. With respect to the present invention, use is made of a blackbody device that acts as an "emitter" for detecting a fault in the laser energy delivery system and signaling by blackbody radiation feedback that a change in the intensity of the laser energy has occurred.

A better shut-off device for laser energy delivery systems, as defined by the present invention, is needed in order to provide improved sensitivity in the detection of overheating. The power per unit area or "emittance" (M) radiating from the surface of a blackbody is defined as being proportional to the 4th power of its temperature by formula:

$$M = sT^4$$

where s is the Stefan-Boltzmann constant and T is temperature measured in Kelvin. Thus, if the temperature is doubled, the emittance increases by a factor of 16. This exactness in emittance measurement for a blackbody means that the use of a blackbody as an emitter would provide greater sensitivity, precision and accuracy than other substances in measuring changes in emittance due to a fault in an energy delivery system. Other substances which are not ideal absorbers would be slower in signaling a change in absorbed energy, since they lose energy by one or more of the following means: transmittance through the substance, reflection from its surface, or scattering at voids between its particles.

The term "emitter," as used herein, refers to a material, i.e. metal or alloy, with an emissivity value greater than 0.10 at wavelengths between 1.1 to about 2.2 micrometers. Preferable, the emissivity values would be greater than 0.20. More preferable, the emissivity values would be greater than 0.40.

A metallic object is a good emitter since the electrons move freely throughout the object and oscillate with large amplitude in response to the electrical field of an incoming light wave. The radiation from the oscillating electrons is seen as reflected light with some of the incoming radiation actually being absorbed. In a preferred embodiment, the emitter used in the present invention is metallic, such as a wire. The metal may be selected from, but not limited to, the group comprising stainless steel, alumel, brass, bronze, chromel, chromium, cobalt, constantan, copper, inconel, iron, manganese, molybdenum, monel, nichrome, nickel, tantalum, titanium, tungsten, vanadium, and zinc. In a preferred embodiment, the metal is stainless steel. Stainless steel is not only a good emitter, but has a history of being useful in medical devices, can be purchased as medical grade, and is malleable making it easy to braid or mold into a specific shape. In another embodiment, the emitter is copper.

The emitter may be positioned in various locations relative to the optical fiber including proximal to, bonded to, incorporated within, or at a fixed distance from the optical fiber. In another embodiment, the emitter coats the optical fiber. In yet another embodiment, the emitter is incorporated into the buffer of the optical fiber. The optical fiber is surrounded by an inner polymer, a cladding, and an outer polymer, a buffer, and the emitter may be incorporated into the buffer.

In one embodiment, the present invention is drawn to a self-monitoring catheter that can effectively detect a fault along an optical path and efficiently shut down the assembly. The methods of the invention can be used to reduce risk due to faults in the optical assembly to both the patient and treatment provider. The light transmitting optical fiber transmits the energy from an energy source which is in communication with the optical fiber. The emitter transmits the radiation from a fault sight back to the optical fiber. The catheter can be any hollow instrument capable of penetrating body tissue or interstitial cavities and providing a conduit for selectively injecting a solution or gas, including without limitation, venous and arterial conduits of various sizes and shapes, bronchioscopes, endoscopes, cystoscopes, culpascopes, colonscopes, trocars, laparoscopes and the like. Catheters of the present invention can be constructed with biocompatible materials known to those skilled in the art, e.g., silastic, polyethylene, Teflon, polyurethanes, etc. The solution includes those solutions, e.g., aqueous solutions, which can be administered to a subject through a device of the present invention. The solution may be a cooling fluid or irrigation fluid. In particular, the solution should not diminish the strength, quality, or wavelength of energy emitted, e.g., laser energy, from the optical apparatus. The solution may be a pharmaceutically acceptable carrier or vehicle. The catheter consists of at least one lumen. The optical fiber and the emitter may be contained within the same lumen as the solution or in a separate lumen.

In one embodiment, the optical apparatus of the invention is typically positioned proximal to the tissue targeted for treatment within a catheter. The catheter has been positioned proximate to the targeted tissue site and provides that the optical apparatus can be slidably positioned proximate to the tissue, thereby avoiding direct contact with the tissue and/or body fluids. Light energy is then passed through the optical apparatus onto the targeted tissue such that it is absorbed which causes ablation, coagulation and/or phototherapeutic processes to occur within the tissue. Faults in the optical fiber are directly monitored by sensing the emission from the emitter which is optically coupled to the fiber. Once a fault is detected the light energy can be automatically shut off preventing damage to the catheter, the patient, or the treatment provider. For example, the present invention provides eye safety. This is particularly advantageous when the site is internal to the patient because safety goggles can be avoided by the staff. In one embodiment, the optical fiber is positioned within a lumen formed by a flexible or rigid elongate member. In another embodiment, the optical fiber can be slidably controlled within the lumen such that positioning of the optical fiber within the elongate member is readily achieved.

This invention is further illustrated by the following descriptions of the figures which should not be construed as limiting. The contents of all references, patents and published patent applications cited throughout this application, are incorporated herein by reference.

Figure 1A:
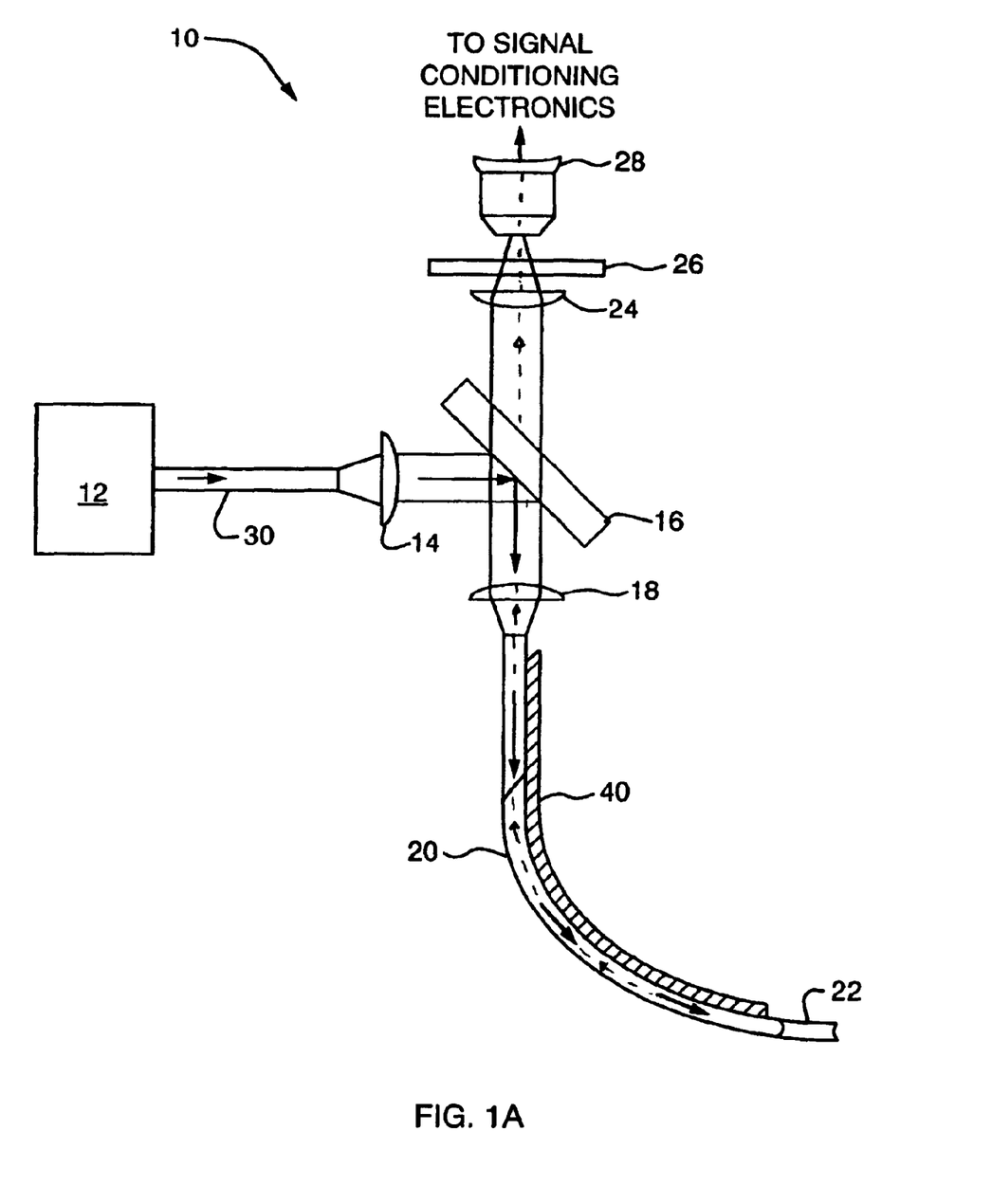
FIG. 1A is a schematic diagram illustrating an optical system in accordance with the present invention depicting the emitter bonded to the optical fiber.
Figure 1B:
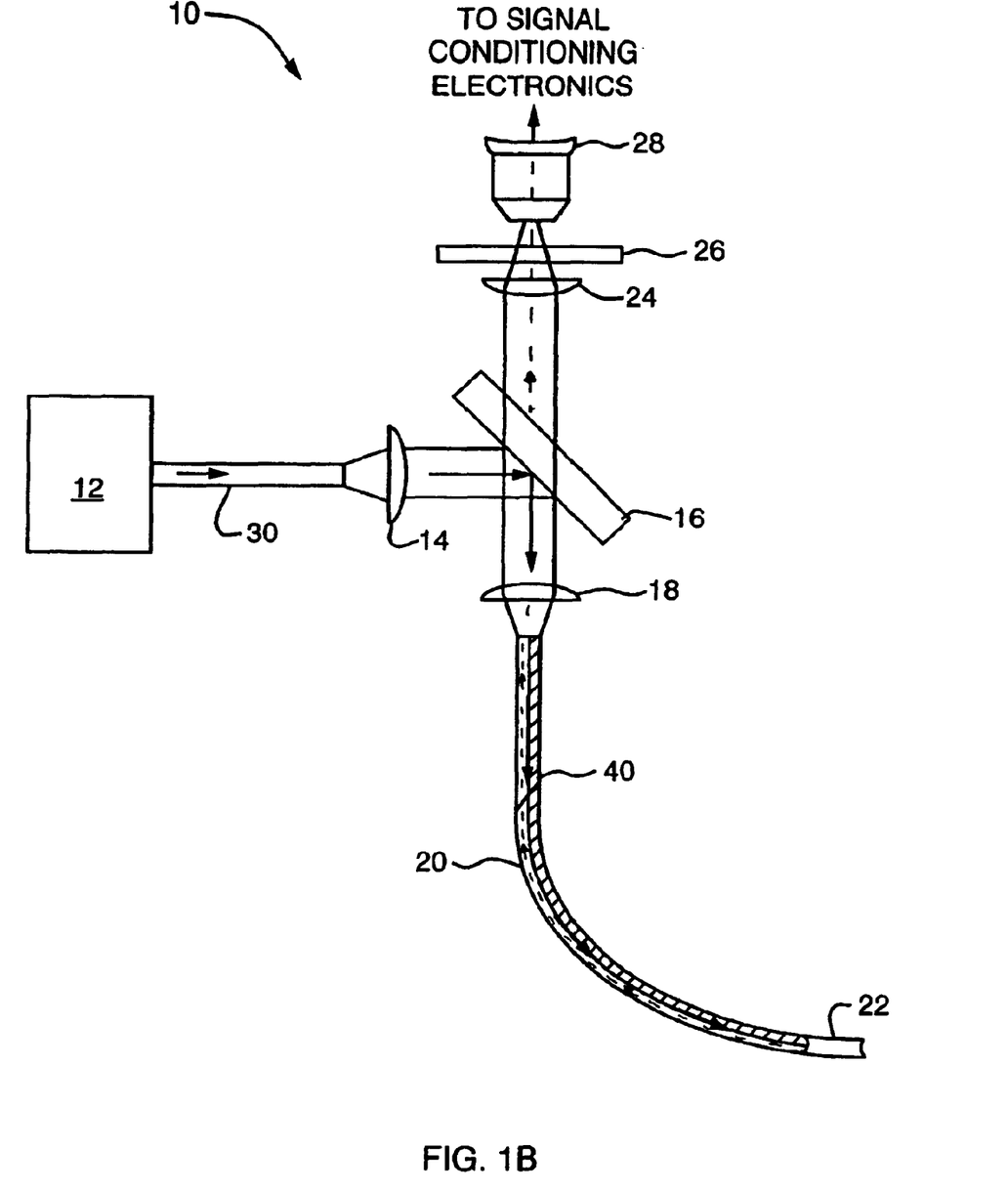
FIG. 1B is a schematic diagram illustrating an optical system in accordance with the present invention depicting the emitter incorporated into the optical fiber.
Figure 1C:
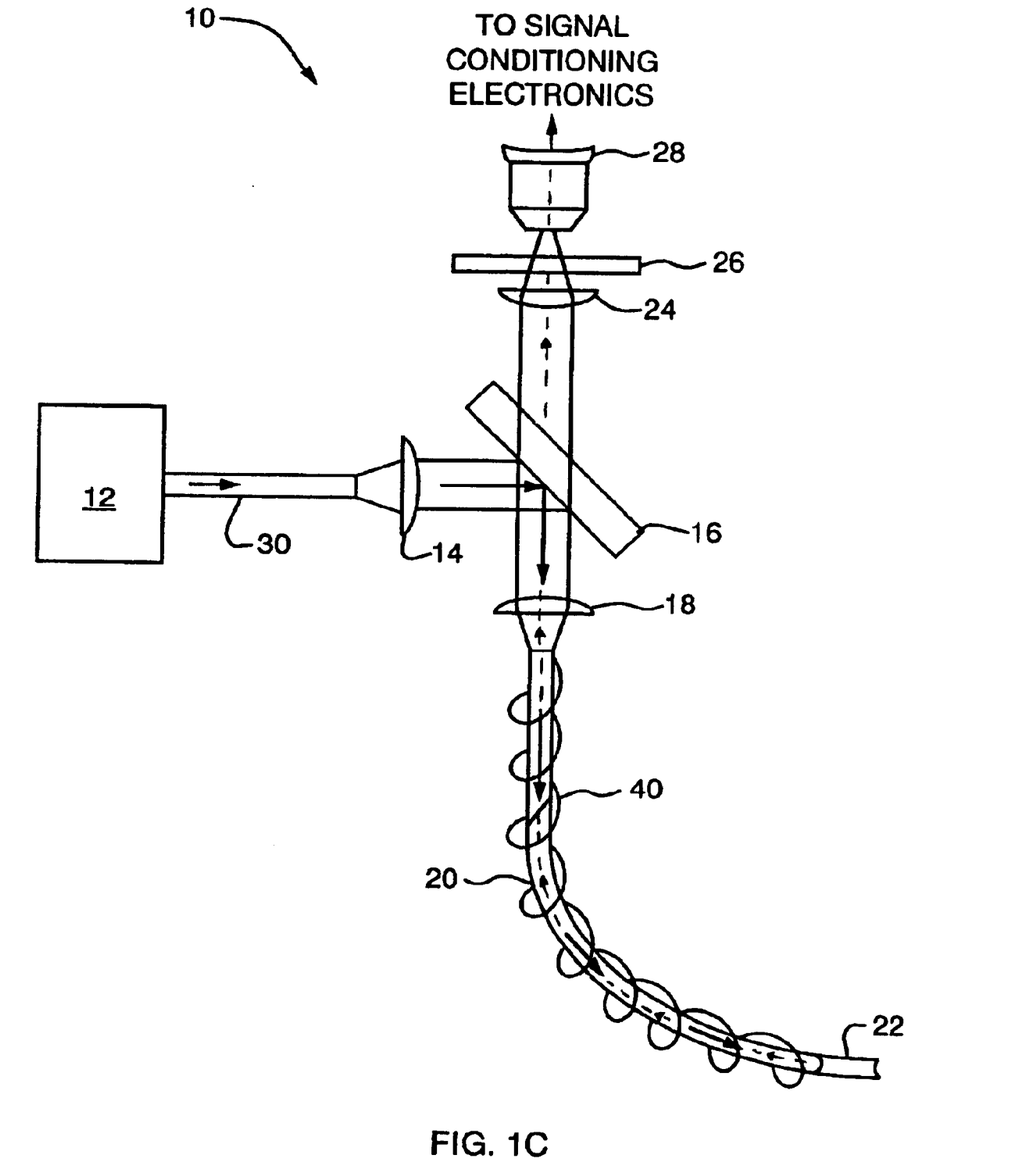
FIG. 1C is a schematic diagram illustrating an optical system in accordance with the present invention depicting the emitter spiraled around the optical fiber.

FIG. 1 illustrates an optical system 10 in accordance with the present invention having a laser source 12 in communication with an optical fiber 20. The laser source 12 can be any laser having any known form of lasing medium such as, for example, Ho:YAG, Nd:YAG, $CO_2$, dye, or He—Ne lasing medium. One preferred laser is a 980 nanometer diode laser (Applied Optronics Corporation, Plainville, N.J.). The optical system 10 can also include a collimating lens 14, a beam splitter 16, first and second optical fibers 20, 30, first and second focusing lenses 18, 24, a filter 26, and a detector 28. The laser source 12 can emit a laser beam that is projected, for example, through a first optical fiber 30 to a collimating lens 14, which further collimates or improves the quality of the beam. The laser beam can then be deflected 90° by a beam splitter 16, and further projected, e.g., by lens 18, to an optical fiber 20. The light source emerging from the optical fiber 20 at the distal end 22 of the optical system 10 can then be used for phototherapy.

The emitter, 40, can be positioned in a variety of locations along the optical fiber. Non-limiting examples of the position of the emitter in relation to the optical fiber are depicted in FIGS. 1A, 1B, and 1C. The emitter may be disposed along the length of the optical fiber (see FIG. 1A), incorporated into the optical fiber (see FIG. 1B), or spiraled around the optical fiber (see FIG. 1C). The emitter may be a wire, a network of metallic fibers, or a coating on the optical fiber. The emitter may be a continuous or noncontinuous element disposed along the length of the optical fiber. The emitter may be wrapped around all or part of the optical fiber. The emitter may be bonded to the optical fiber, proximal to the optical fiber, at a fixed distance from the optical fiber, or coat the optical fiber.

The collimating lens 14, and the first and second focusing lenses can be, for example, molded aspheric lenses. While a variety of different lenses can be used, aspheric lenses tend to deliver better optical performance and image quality than traditional spherical lenses. Because aspheric lenses bend light rays more precisely than traditional spherical lenses, the laser light is more precisely directed toward and reflected off of the beam splitter. Aspheric lenses also keep the temperatures low inside the beam splitter box, while at the same time allowing for high-powered transmission of the laser light.

The beam splitter 16, or partially reflective mirror, can be disposed at a predetermined angled, such as, for example, a 45° angle, in the laser beam path to reflect a portion of the light falling on it. A wide variety of beam splitters can be employed as beam splitter 16. By way of non-limiting example, a dichroic filter arranged for substantial or maximum reflection of incident laser beam energy within a defined spectral range can be used. The laser beam from the laser source 12 is reflected by the beam splitter 16 toward the second focusing lens 18 and the optical fiber 20. In one embodiment, where laser source 12 can be a Nd:YAG laser, generating a high power, low divergence beam at a 1.06 micrometer wavelength, the beam splitter 16 can be chosen to reflect laser energy having a wavelength of less than about 1.1 micrometers. Alternatively, if the laser is a diode laser operating at 980 nanometers, the beamsplitter can be chosen to reflect light at wavelengths less than about 1.0 micrometers.

Once the laser energy from the laser source 12 is reflected off of the beam splitter 16, the laser beam can pass through a second focusing lens 18 to the optical fiber 20. The laser beam then travels to the distal end 22 of the optical system 10 for application to the treatment site. During treatment, some blackbody radiation is likely to be produced. This radiation (which is typically at wavelengths greater than 1.1 micrometers) travels (shown by the dotted line in FIG. 1) back through the optical fiber 20 to the beam splitter 16 which transmits laser energy having a wavelength greater than 1.1 micrometers, and more particularly, between 1.2 and 2.2 micrometers. Low OH fiber is preferred as it transmits these wavelengths of interest. Once the blackbody radiation is transmitted through the beam splitter 16, it can then pass through a second focusing lens 24 and a filter 26, to an optical detector 28.

Figure 2:
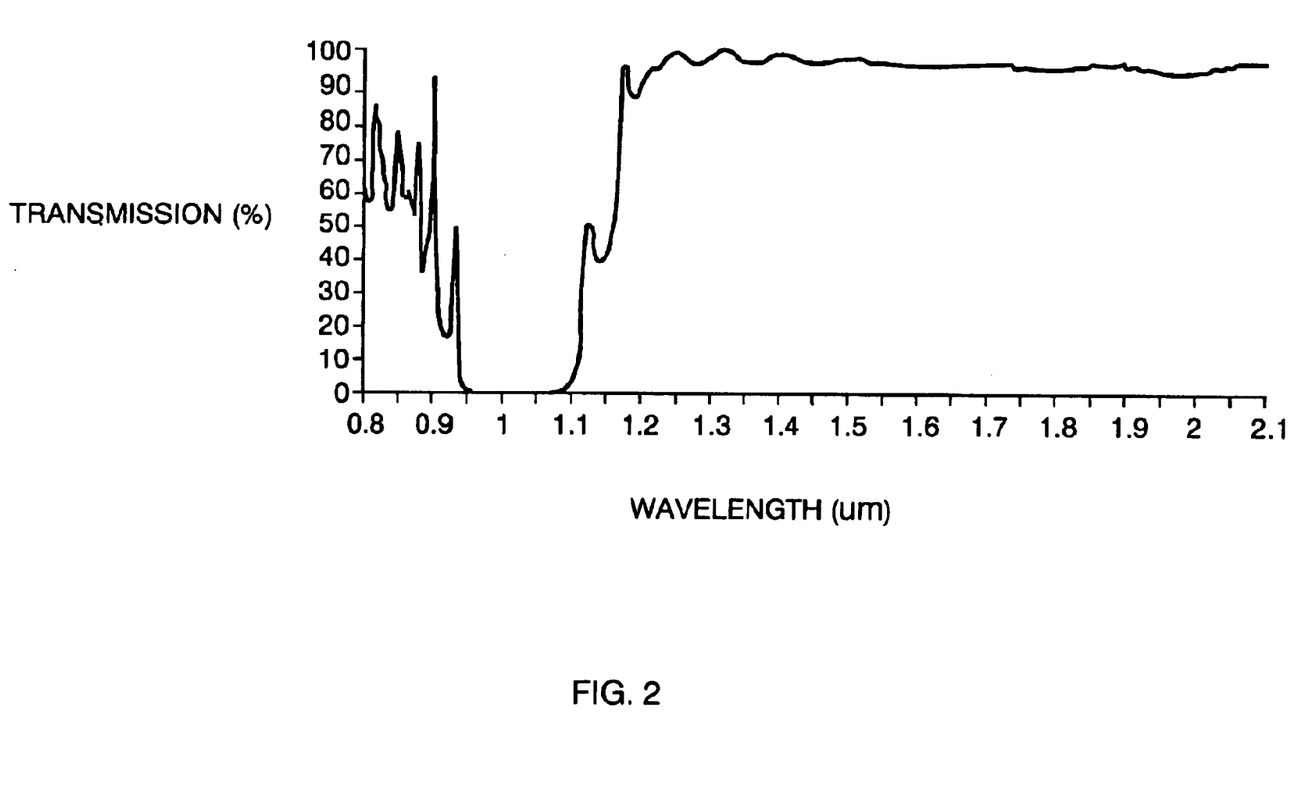
FIG. 2 is a graph showing the transmissivity through an illustrative beamsplitter at various wavelengths in accordance with the present invention.

FIG. 2 is a chart showing the percent transmission at different wavelengths. With a Nd:YAG laser system, for example, the beam splitter reflects 99.98% of laser light at the therapeutic wavelength at 1.06 micrometers and transmits only 0.3% of laser light at wavelengths below 1.1 micrometers. The 0.03% of laser light that is transmitted at wavelengths below 1.1 micrometers is blocked by a high rejection notch filter 26. Thus, emitted blackbody radiation at wavelengths greater than 1.1 micrometers is selectively passed through both the beam splitter 16 and the notch filter 26 to the detector 28.

Figure 3:
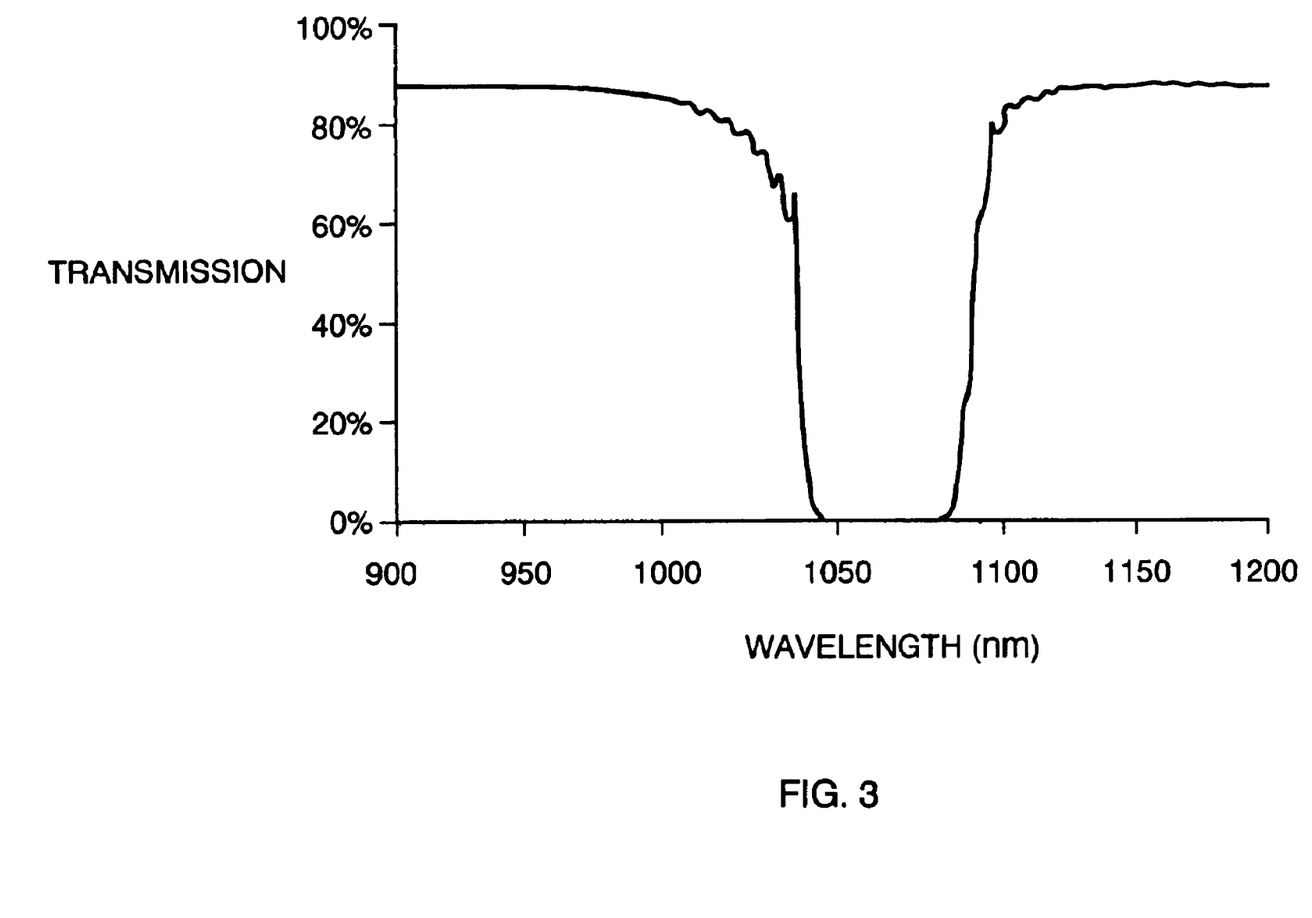
FIG. 3 is a graph showing the transmissivity of an illustrative notch filter at specific wavelengths.

The notch filter 26 can be, for example, a holographic notch filter designed for Raman spectroscopy. As illustrated in FIG. 3, the notch filter 26 can transmit laser light having a wavelength above about 1080 nanometers and below about 1040 nanometers. Thus, any laser light passing through the beam splitter having a wavelength of around 1064 nanometers will be blocked by the notch filter 26. Alternatively, with a diode laser operating at 980 nanometers, a dielectric notch filter can selectively block radiation in a spectrum from about 960 nanometers to about 1000 nanometers.

Figure 4:
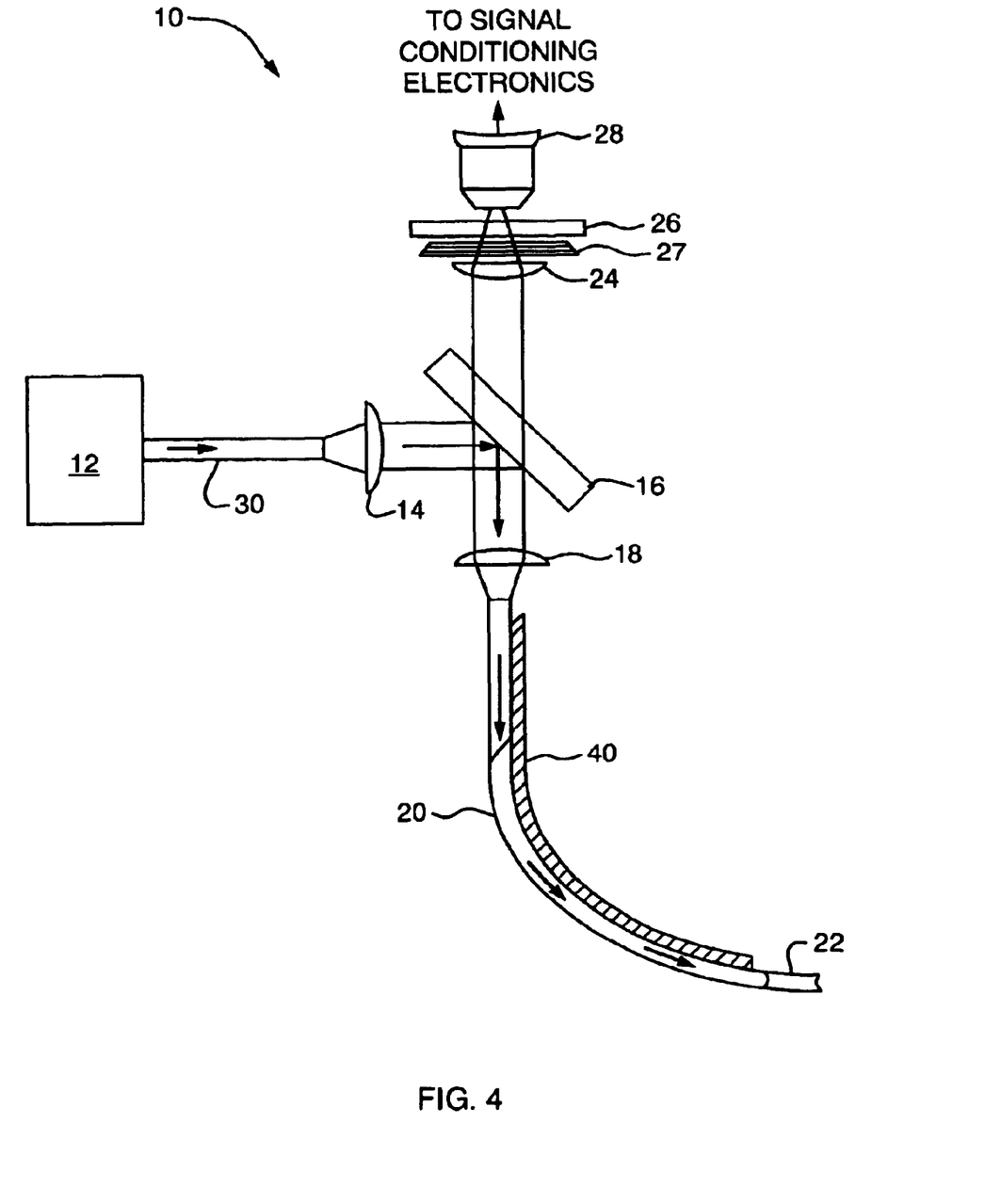
FIG. 4 is a schematic diagram of another optical system in accordance with the invention having several reflecting mirrors.
Figure 5:
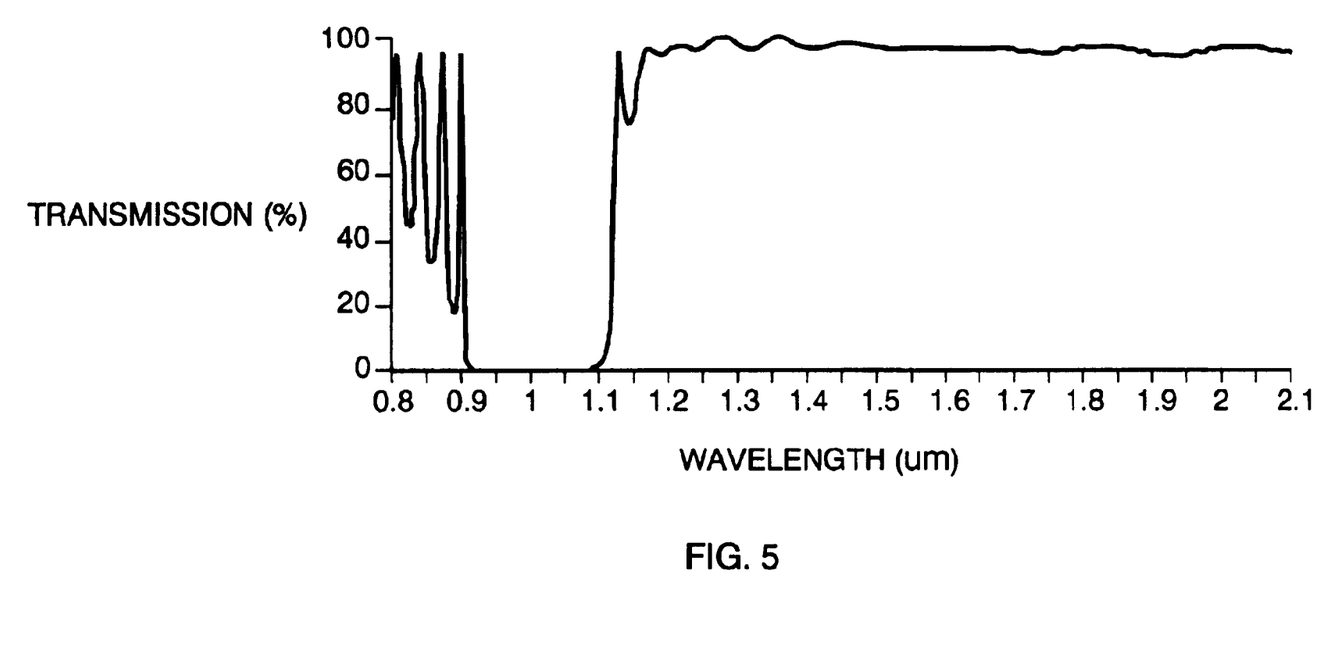
FIG. 5 is graph of transmissivity at various wavelengths through a mirror filter in accordance with the present invention.

The therapeutic waveguide radiation incident on the detector 28 can be further attenuated by the placement of at least one, preferably three or more, 1064 nanometer (or 980 nanometer) laser mirrors 27 placed in the optical path as shown in FIG. 4. Such laser mirrors are available, for example, from Spectrum Thin Films (Bohemia, N.Y.). The mirrors 27 further minimize the amount of reflected light of the therapeutic wavelength. FIG. 5 illustrates the effect of the mirrors 27 on transmission of 1.06 micrometer light. Laser light having wavelengths below 0.9 micrometers and above 1.1 micrometers are transmitted, while light at 1.06 micrometers is almost entirely reflected. Any remaining light at the therapeutic wavelength that still reaches the detector 28 can be treated as an "offset," as discussed further below.

Figure 6:
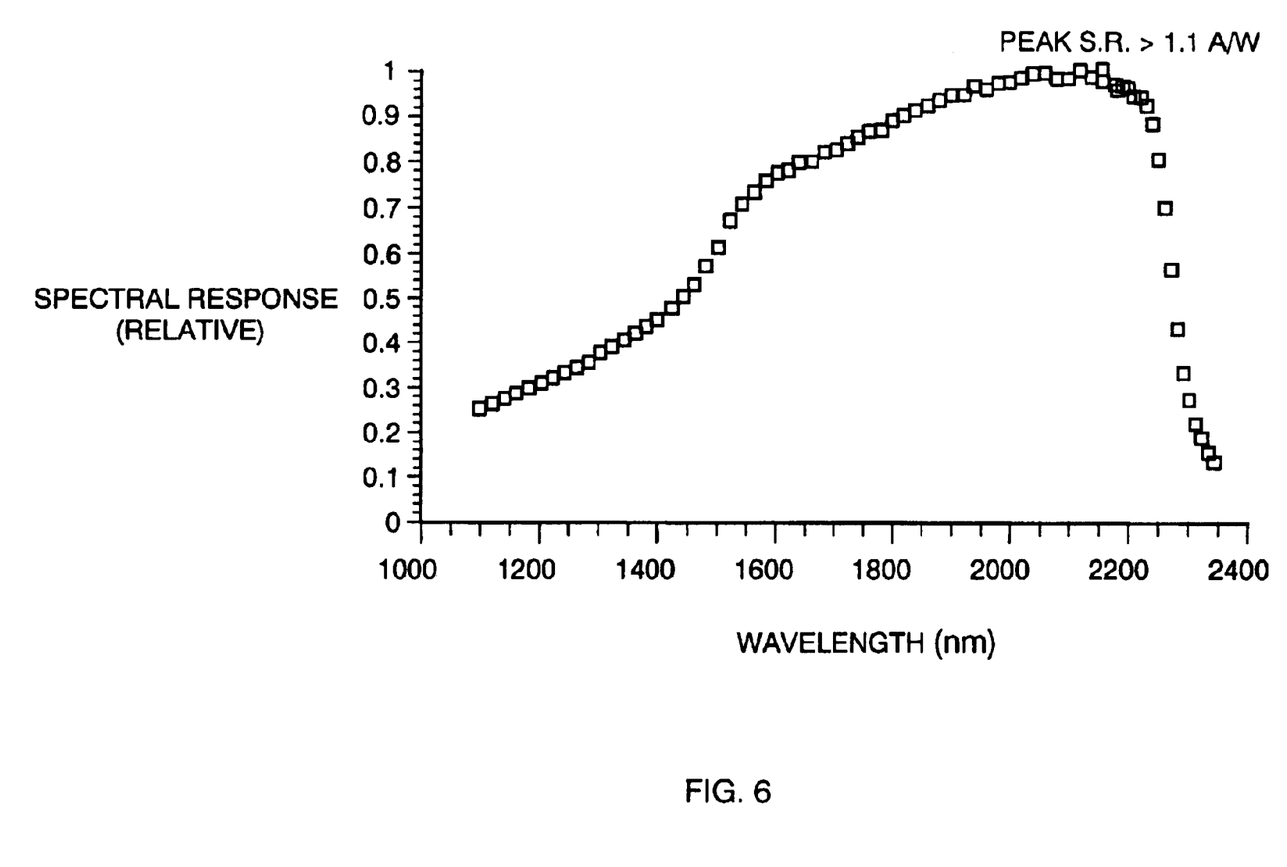
FIG. 6 is a graph showing the spectral response of an illustrative detector at specific wavelengths.

Once the blackbody radiation released by the emitter and transmitted back to the optical fiber passes through the filter 26, it is measured by the optical detector 28. The detector 28 generates a signal which is indicative of the magnitude of blackbody radiation received by the detector. Any one of numerous infrared detectors known in the art can be used. For example, an extended range InGaAs detector, such as the model FD1000 detector made by Fermionix, Inc. (Simi Valley, Calif.), which can detect blackbody radiation having a wavelength between about 1200 nanometers to 2200 nanometers, can be used. The spectral response of an extended range InGaAs detector is shown in FIG. 6.

The detector converts the blackbody radiation released by the emitter into an electrical signal which is then conducted to a signal processor (as shown schematically in FIG. 1). Again, a wide variety of signal processing circuits, as known in the art, can be employed. Generally speaking, the signal processor can include an input terminal, an amplifier for amplifying the signals, analyzing circuitry and an output terminal. In one embodiment, a high gain, low pass current amplifier can be used for a first gain stage, and a voltage amplifier with moderate gain for a second gain stage. An automatic offset adjustment can be used to overcome any offset imposed by the presence of laser energy at the 1.064 micrometer wavelength that is not removed by the filter 26 or reflected by the additional mirrors 27. The output can include a control signal used to interrupt the output of light from the light source 12. When excessive blackbody radiation is detected, the control signal will shut-off transmission of the laser from the laser source 12 thereby preventing device failure.

Figure 7:
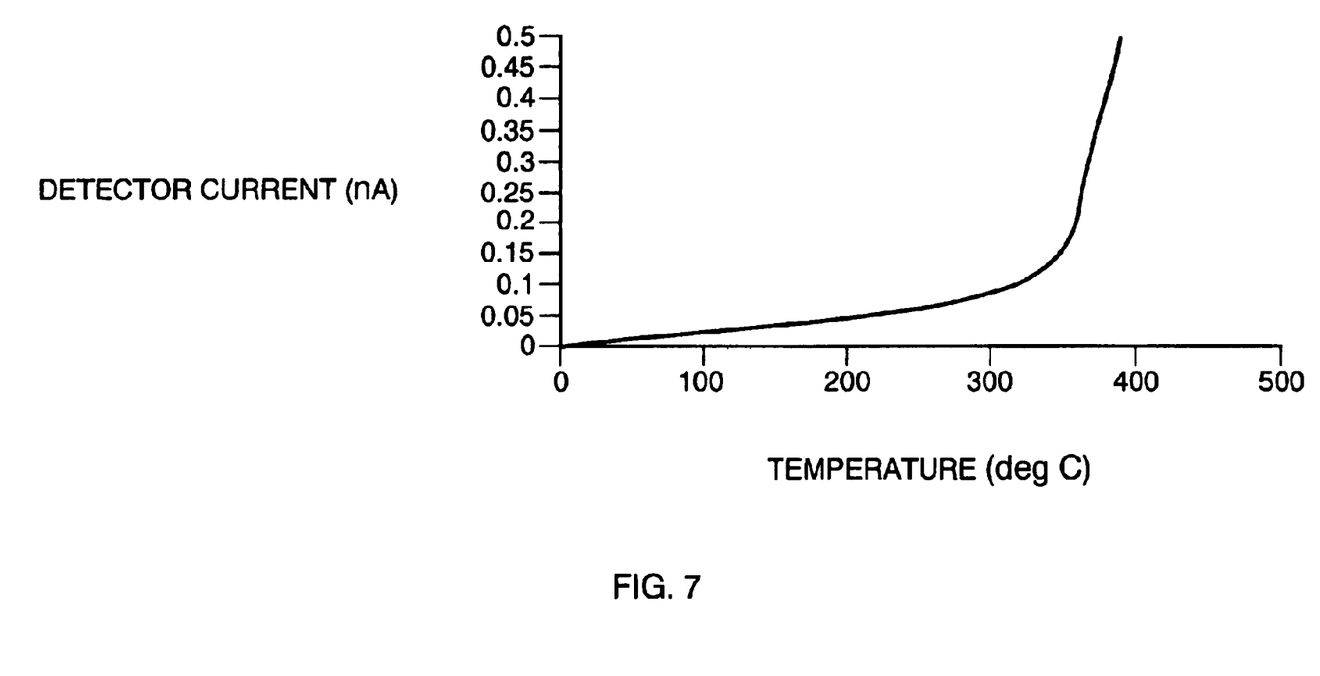
FIG. 7 is a graph showing the variability in output of an illustrative detector when monitoring blackbody radiation from an object at various temperatures.

FIG. 7 illustrates the response of an InGaAs detector to thermal radiation. The detector current was measured as a function of temperature. The average spectral response over the 1.2 to 2.2 micrometer wavelength range is about 0.8 A/W. The measured detector current is about 0.1 nanoamps at 315° C. which corresponds to the 0.125 nanowatts of blackbody radiation incident on the detector.

Figure 8:
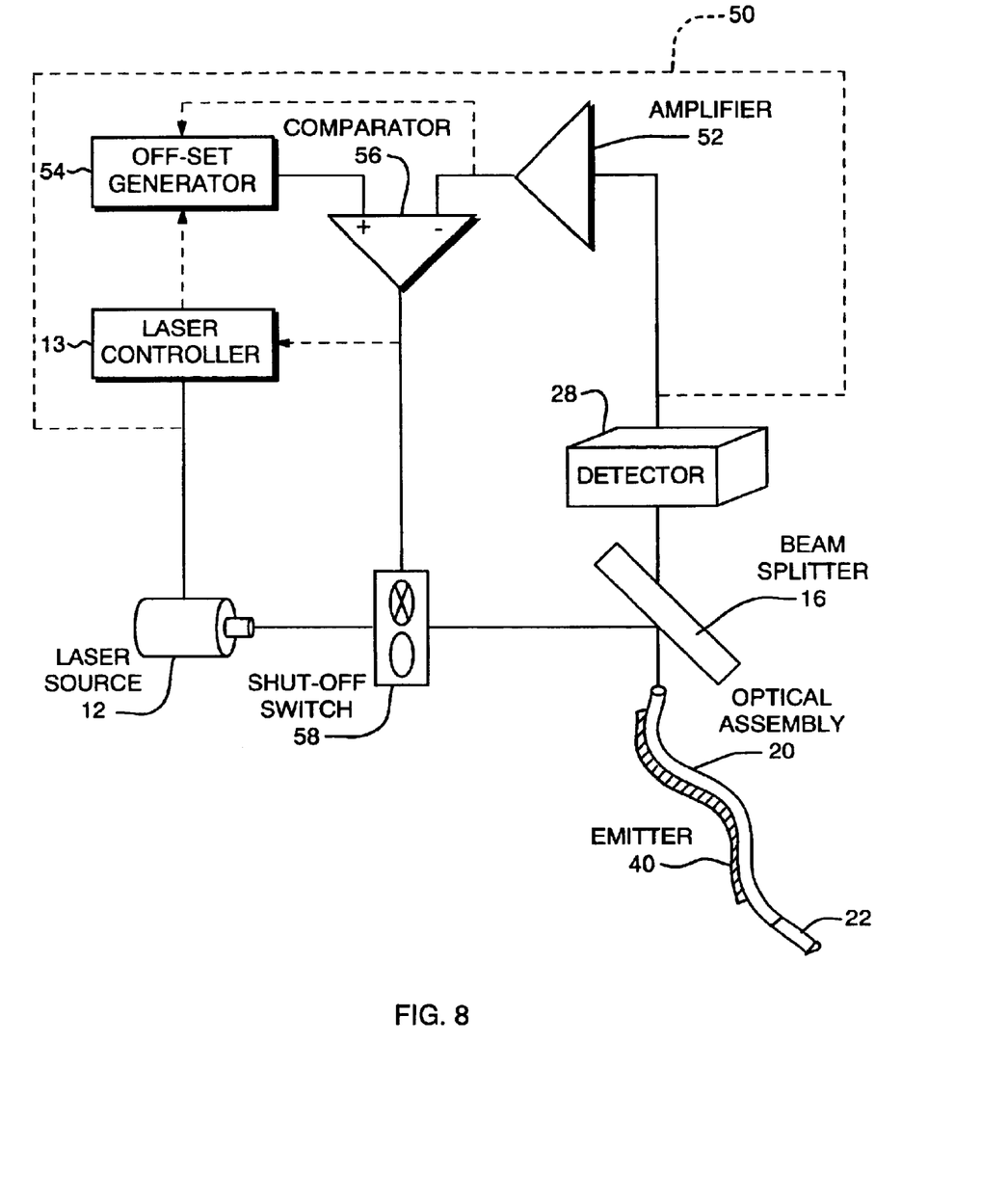
FIG. 8 is a schematic diagram of a signal processor for use in accordance with the present invention.

FIG. 8 is a schematic diagram of a monitoring system according to the invention whereby a measured signal from detector 28 can be used to activate a shut-off shutter 58 or other automatic shut-off element. The control elements described herein can be separately implemented as discrete components or implemented in software. For example, offset generator 54, laser controller 13, amplifier 52 and comparator 56 can be implemented as part of a programmed microprocessor 50.

The measured signal for detector 28 can be amplified by amplifier 52. This amplified measured value can then be compared with a offset value established to offset generator 54 via comparator 56. If the measured value exceeds the offset value a control signal is generated to activate shutter switch 58 and/or the laser controller 13. In some applications, a separate shutter mechanism may not be necessary and the control signal can be used to simply deactivate the laser. The offset generator 54 can be operated manually, automatically or dynamically.

Figure 9:
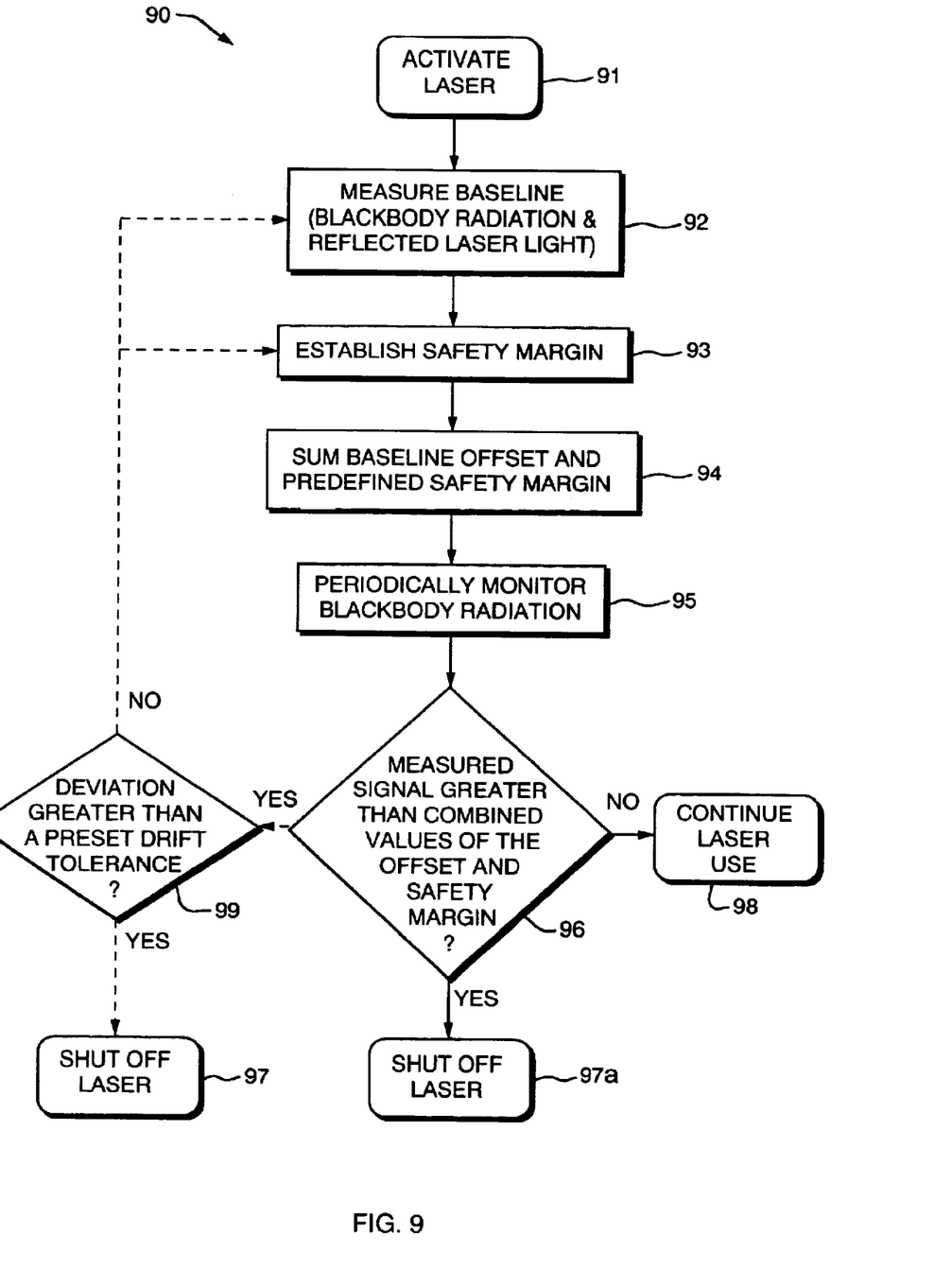
FIG. 9 is a flow diagram illustrating a method of dynamically establishing an offset value in accordance with the present invention.

FIG. 9 is a flow diagram illustrating one method of dynamically establishing a baseline offset value. The flow diagram 90 illustrates one method of monitoring reflected energy. In block 91 the laser is activated. In block 92 a baseline signal, which includes blackbody radiation and reflected laser light, is measured (e.g. by standard sample and hold averaging circuitry). This baseline value may primarily be due to detection of a small amount of radiation at the therapeutic wavelength that is not removed by the filter elements of the invention. This measurement establishes a baseline. Next, as illustrated in block 93, a safety margin is established. This safety margin can be set by the user, predefined based on prior testing established by empirical data, or dynamically determined.

In block 94, the baseline offset value and the safety margin value are summed. The system then periodically measures blackbody radiation during operation (block 95) and compares the measured value with the combined safety margin and offset value (block 96). In the simple embodiment, this comparison will generate a shut-off signal (block 97) if the limit is exceeded or allow continued operation (block 98) if the measured value falls short of the limit.

The system can also, optionally, permit a degree of (upward) drift in the measured signal to accommodate inherent changes in either the detector sensitivity or the ambient heat environment over time. As shown in block 99, the system can further consider whether or not a measured value that exceeds the limit has a deviation that is greater than a preset drift tolerance. If the measured value (or time-averaged sample value) deviates by a large amount (e.g. an energy spike) this would likely be a precursor to device failure and, hence, result in a shut-off signal (block 97A). However, if the deviation is within a preset drift tolerance, the new value can be used to re-establish the safety margin (or baseline) value.

In an alternative embodiment (not shown), the baseline value can also be used to adjust the measured signal, rather than the safety margin. Instead of adding the baseline offset to the predefined safety margin (block 94), the baseline can be subtracted from the monitored reflectance. The adjusted monitored reflectance can then be compared to the safety margin. If the value of the adjusted monitored reflectance exceeds the safety margin, a shut-off signal will be generated.

Additional techniques for monitoring reflected energy in phototherapy devices can be found in U.S. Pat. No. 4,385,832 issued to Doi et al.; U.S. Pat. No. 4,543,477 issued to Doi et al.; U.S. Pat. No. 4,663,520 issued to Tanaka et al.; U.S. Pat. No. 5,012,087 issued to Rockstroh et al.; U.S. Pat. No. 5,057,099 issued to Rink; U.S. Pat. No. 5,104,391 issued to Ingle et al.; U.S. Pat. No. 5,499,313 issued to Kleinerman; and U.S. Pat. No. 5,154,707 issued to Rink et al.

While the present invention has been described in connection with a medical therapeutic apparatus, it is to be understood that the methods and systems of the present invention may be applied to any laser apparatus. One of ordinary skill in the art will know, or be able to ascertain, using no more than routine experimentation, many equivalents to the specific embodiments of the invention described herein. These and all other equivalents are intended to be encompassed by the following claims. All publications and references cited herein are expressly incorporated herein by reference in their entirety.

What is claimed is:

1. A monitoring apparatus for detecting a fault in a phototherapy device having at least one optical fiber defining an optical path between a source of therapeutic radiation and a treatment site, the apparatus comprising:
    a metallic blackbody radiation emitter disposed along the optical-fiber, for absorbing therapeutic radiation released at a fault and entitling blackbody radiation at wavelengths between 1.1 and 2.2 micrometers,
    a detector optically coupled to the optical fiber for receiving blackbody radiation,
    whereby therapeutic radiation released at the fault can be detected by measurement of blackbody radiation emitted by the emitter and transmitted by the fiber to the detector.

2. The apparatus of claim 1, wherein the emitter further comprises an emissivity value greater than 0.10 at wavelengths between 1.1 and 2.2 micrometers.

3. The apparatus of claim 1, wherein the emitter is a wire.

4. The apparatus of claim 1, wherein the emitter comprises metallic particles.

5. The apparatus of claim 1, wherein the emitter is a continuous element disposed along the length of the optical fiber.

6. The apparatus of claim 1, wherein a plurality of emitters is disposed at discrete locations along the length of th optical fiber.

7. The apparatus of claim 1, wherein the emitter is proximal to the optical fiber.

8. The apparatus of claim 1, wherein the emitter is bonded to the optical fiber.

9. The apparatus of claim 1, wherein the emitter is disposed at a fixed distance from the optical fiber.

10. The apparatus of claim 1, wherein the emitter coats the optical fiber.

11. The apparatus of claim 1, wherein the optical fiber is surrounded by an inner polymer, a cladding, and an outer polymer, a buffer, and the emitter is incorporated into the buffer.

12. The apparatus of claim 1, wherein the emitter is selected from the group comprising stainless steel, alumel, brass, bronze, chromel, chromium, cobalt, constantan, copper, inconel, iron, manganese, molybdenum, monel, nichrome, nickel, tantalum, titanium, tungsten, vanadium, and zinc.

13. The apparatus of claim 1, wherein the apparatus further comprises at least one filter disposed along the optical path for blocking the wavelength of the therapeutic radiation and selectively transmitting blackbody radiation.

14. The apparatus of claim 13, wherein the filter further comprises a beam splitter that is reflective at a therapeutic wavelength and transmissive for at least one blackbody radiation wavelength distinct from the therapeutic wavelength.

15. The apparatus of claim 1, wherein the phototherapy device is a laser surgical instrument.

16. The apparatus of claim 1, wherein the apparatus further comprises an offset generator, for establishing an offset value, and a comparator, for comparing a measured value and the offset value in order to determine when the intensity of transmitted blackbody radiation has exceeded a threshold established by the offset value.

17. The apparatus of claim 16, wherein the comparator generates a control signal and the apparatus further comprises an alarm responsive to the control signal to alert the user that the threshold has been exceeded.

18. The apparatus of claim 16, wherein the comparator generates a control signal and the apparatus further comprises a shut-off switch responsive to the control signal to terminate phototherapy when the threshold has been exceeded.

19. The apparatus of claim 18, wherein the shut-off switch further comprises a shutter that blocks the therapeutic laser radiation.

20. A self-monitoring catheter for performing phototherapy procedures comprising:
    an elongate body, adapted for insertion into a subject, having one of more inner lumens;
    at least one optical fiber defining an optical path between a source of therapeutic radiation and a treatment site having a proximal and adapted for coupling to an optical beam splitter such that forward propagating radiation can be transmitted into the fiber from the source and backward propagating radiation can be directed to a detector; and
    a metallic blackbody radiation emitter disposed along the optical-fiber, for absorbing therapeutic radiation released at a fault and emitting blackbody radiation at wavelengths between 1.1 and 2.2 micrometer,
    whereby therapeutic radiation released at the fault can be detected by measurement of blackbody radiation emitted by the emitter and transmitted by the fiber to a detector.

21. The catheter of claim 20, wherein one or more of the inner lumens is a conduit for a fluid.

22. The catheter of claim 21, wherein one or more of the inner lumens is a conduit for an irrigating fluid.

23. The catheter of claim 21, wherein one or more of the inner lumens is a conduit for a cooling fluid.

24. The catheter of claim 21, wherein the fluid is separate from the emitter.

25. The catheter of claim 20, wherein the emitter further comprises an emissivity value greater than 0.10 at wavelengths between 1.1 and 2.2 micrometers.

26. The catheter of claim 20, wherein the emitter is a wire.

27. The catheter of claim 20, wherein the emitter comprises metallic particles.

28. The catheter of claim 20, wherein the emitter is a continuous element disposed along the length of the optical fiber.

29. The catheter of claim 20, wherein a plurality of emitters is disposed at discrete locations along the length of the optical fiber.

30. The catheter of claim 20, wherein the emitter is proximal to the optical fiber.

31. The catheter of claim 20, wherein the emitter is bonded to the optical fiber.

32. The catheter of claim 20, wherein the emitter is disposed at a fixed distance from the optical fiber.

33. The catheter of claim 20, wherein the emitter coats the optical fiber.

34. The catheter of claim 20, wherein the optical fiber is surrounded by an inner polymer, a cladding, and an outer polymer, a buffer, and the emitter is incorporated into the buffer.

35. The catheter of claim 20, wherein the emitter is selected from the group comprising stainless steel, alumel, brass, bronze, chromel, chromium, cobalt, constantan, copper, inconel, iron, manganese, molybdenum, monel, nichrome, nickel, tantalum, titanium, tungsten, vanadium, and zinc.

36. A monitoring apparatus for detecting a fault in a phototherapy device having at least one optical fiber defining an optical path between a source of therapeutic radiation and a treatment site, the apparatus comprising:
    a blackbody radiation emitter disposed along the optical path, for absorbing therapeutic radiation released at a fault and emitting blackbody radiation, wherein the emitter comprises a network of metallic fibers,
    a detector optically coupled to the optical fiber for receiving blackbody radiation,
    whereby therapeutic radiation released at the fault can be detected by measurement of blackbody radiation emitted by the emitter and transmitted by the fiber to the detector.

37. A monitoring apparatus for detecting a fault in a phototherapy device having at least one optical fiber defining an optical path between a source of therapeutic radiation and a treatment site, the apparatus comprising:
    a blackbody radiation emitter disposed along the optical path, for absorbing therapeutic radiation released at a fault and emitting blackbody radiation, wherein the emitter is a wire wrapped around the optical fiber,
    a detector optically coupled to the optical fiber for receiving blackbody radiation,
    whereby therapeutic radiation released at the fault can be detected by measurement of blackbody radiation emitted by the emitter and transmitted by the fiber to the detector.

38. A monitoring apparatus for detecting a fault in a phototherapy device having at least one optical fiber defining an optical path between a source of therapeutic radiation and a treatment site, the apparatus comprising:
    a blackbody radiation emitter disposed along the optical path, for absorbing therapeutic radiation released at a fault and emitting blackbody radiation, wherein the emitter comprises a plurality of metallic fibers at least partially surrounding the optical fiber,
    a detector optically coupled to the optical fiber for receiving blackbody radiation,
    whereby therapeutic radiation released at the fault can be detected by measurement of blackbody radiation emitted by the emitter and transmitted by the fiber to the detector.

39. A self-monitoring catheter for performing phototherapy procedures comprising:
    an elongate body, adapted for insertion into a subject, having one of more inner lumens, such that one or more of the Inner lumens is a conduit for a fluid,
    at least one optical fiber defining an optical path between a source of therapeutic radiation and a treatment site having a proximal end adapted for coupling to an optical beam splitter such that forward propagating radiation can be transmitted into the fiber from the source and backward propagating radiation can be directed to a detector; and
    a blackbody radiation emitter disposed along the optical path, for absorbing therapeutic radiation released at a fault and emitting blackbody radiation, wherein the fluid is in direct contact with the emitter,
    whereby therapeutic radiation released at the fault can be detected by measurement of blackbody radiation omitted by the emitter and transmitted by the fiber to a detector.

40. A self-monitoring catheter for performing phototherapy procedures comprising:
    an elongate body, adapted for insertion into a subject, having one of more inner lumens;
    at least one optical fiber defining an optical path between a source of therapeutic radiation and a treatment site having a proximal end adapted for coupling to an optical beam splitter such that forward propagating radiation can be transmitted into the fiber from the source and backward propagating radiation can be directed to a detector; and
    a blackbody radiation emitter disposed along the optical path, for absorbing therapeutic radiation released at a fault and emitting blackbody radiation, wherein the emitter comprises a network of metallic fibers,
    whereby therapeutic radiation released at the fault can be detected by measurement of blackbody radiation emitted by the emitter and transmitted by the fiber to a detector.

41. A self-monitoring catheter for performing phototherapy procedures comprising:
    an elongate body, adapted for insertion into a subject, having one of more inner lumens;
    at least one optical fiber defining an optical path between a source of therapeutic radiation and a treatment site having a proximal end adapted for coupling to an optical beam splitter such that forward propagating radiation can be transmitted into the fiber from the source and backward propagating radiation can be directed to a detector; and
    a blackbody radiation emitter disposed along the optical path, for absorbing therapeutic radiation released at a fault and emitting blackbody radiation, wherein the emitter is a continuous wire wrapped around the optical fiber and disposed along the length of the optical fiber, whereby therapeutic radiation released at the fault can be detected by measurement of blackbody radiation emitted by the emitter and transmitted by the fiber to a detector.

42. A self-monitoring catheter for performing phototherapy procedures comprising:
- an elongate body, adapted for insertion into a subject, having one of more inner lumens;
- at least one optical fiber defining an optical path between a source of therapeutic radiation and a treatment site having a proximal end adapted for coupling to an optical beam splitter such that forward propagating radiation can be transmitted into the fiber from the source and backward propagating radiation can be directed to a detector; and
- a blackbody radiation emitter disposed along the optical path, for absorbing therapeutic radiation released at a fault and omitting blackbody radiation, wherein the emitter is a plurality of metallic fibers at least partially surrounding the optical fiber and disposed along the length of the optical fiber,
- whereby therapeutic radiation released at the fault can be detected by measurement of blackbody radiation emitted by the emitter and transmitted by the fiber to a detector.

43. A method for detecting a fault in a phototherapy device having at least one optical fiber defining an optical path between a source of therapeutic radiation and a treatment site, comprising:
- absorbing therapeutic radiation released at a fault along the optical fiber and emitting blackbody radiation at wavelengths between 1.1 and 2.2 micrometers, and
- detecting blackbody radiation emitted from the fault site, whereby therapeutic radiation released at the fault can be detected as blackbody radiation emitted and then transmitted by the optical fiber to the detector.

44. The method of claim 43, wherein the method further comprises generating an offset value.

45. The method of claim 44, wherein the method further comprises comparing the detected blackbody radiation to the offset value in order to determine when the intensity of the detected blackbody radiation has exceeded a threshold established by the offset value.

46. The method of claim 45, wherein the method further comprises alerting the user when the detected blackbody radiation exceeds the offset value.

47. The method of claim 45, wherein the method further comprises shutting off the device when the detected blackbody radiation exceeds the offset value.

48. The method of claim 45, wherein the method further comprises blocking the source of radiation when the detected blackbody radiation exceeds the offset value.

49. The method of claim 43, wherein the method further comprises filtering the therapeutic radiation transmitted alone the optical fiber, for selectively receiving blackbody radiation generated at the fault site.

50. The method of claim 49, wherein the step of filtering the therapeutic radiation transmitted along the optical fiber further comprises providing a beam splitter that is reflective at a therapeutic wavelength and transmissive for at least one blackbody radiation wavelength distinct from the therapeutic wavelength.

* * * * *